United States Patent [19]
Konno et al.

[11] Patent Number: 5,632,980
[45] Date of Patent: May 27, 1997

[54] AIDS THERAPEUTIC AGENTS COMPRISING POLYMERS FORMED FROM CINNAMIC ACID DERIVATIVES

[76] Inventors: Kunio Konno, 1-33-3, Kakinokizaka, Meguro-ku, Tokyo; Hiroshi Sakagami, Chigusadai Danchi 246, 33, Chigusadai, Midori-ku, Yokohama-shi, Kanagawa-ken; Yutaka Kawazoe, 5-14-14, Shimomeguro, Meguro-ku, Tokyo; Naoki Yamamoto, Haramachi Jutaku 501, 3-11, Ebisu Minami, Shibuya-ku, Tokyo, all of Japan

[21] Appl. No.: 982,463

[22] Filed: Nov. 27, 1992

[30] Foreign Application Priority Data

Nov. 27, 1991 [JP] Japan .................. 3-337796

[51] Int. Cl.$^6$ .................. C08F 20/62; A61K 31/765
[52] U.S. Cl. .................. 424/78.31; 514/885; 526/227
[58] Field of Search .................. 514/885, 78.1, 514/78.7; 424/78.37, 78.31

[56] References Cited

U.S. PATENT DOCUMENTS 5,223,258  6/1993  Machida et al. .................. 514/885

OTHER PUBLICATIONS

P. Lai et al., "Modification of Human Immunodeficiency Viral Replication by Pine Cone Extracts", *Aids Research and Human Retroviruses*, vol. 6, No. 2, pp. 205–217 (1990).

Klocking et al., "Gewinnung, Charakterisierung und Antivirale Aktivität von Phenolkorperpolymerisaten", *Pharmazie*, vol. 34, No. 5–6, 1979, pp. 292–295.

Sydow et al., "Zur Wirkung von Phenolkörperpolymerisaten auf Retroviren", *Pharmazie*, vol. 41, No. 12, 1986, pp. 865–868.

Hils et al., "Hemmung ausgewählter Influenzavirusstämme der Typen A und B durch Phenolkörperpolymerisate", *Biomedica Biochimica Acta*, vol. 45, No. 9, 1986, pp. 1173–1179.

Sakagami et al., "Lignified Materials as a Potential Medicinal Resource. IV. Dehydrogenation Polymers of Some Phenylpropenoids and Their Capacity to Stimulate Polymorphonuclear Cell Iodination", *Chem. Pharm. Bull.*, vol. 39, No. 4, 1991, pp. 950–955.

*Primary Examiner*—Peter F. Kulkosky
*Attorney, Agent, or Firm*—Oliff & Berridge

[57] ABSTRACT

AIDS therapeutic agents are provided which are less toxic, have a strong anti-AIDS virus activity and comprise as an effective ingredient a dehydrogenation polymer of a cinnamic acid derivative having a phenyl group substituted with at least one hydroxyl group or a pharmaceutically acceptable salt thereof.

35 Claims, 3 Drawing Sheets

AIDS THERAPEUTIC AGENTS COMPRISING POLYMERS FORMED FROM CINNAMIC ACID DERIVATIVES

BACKGROUND OF THE INVENTION

1. Field of the Invention

The present invention relates to AIDS therapeutic agents containing a dehydrogenation polymer of a substituted cinnamic acid as an effective ingredient. More particularly, it is concerned with AIDS therapeutic agents comprising a dehydrogenation polymer of a cinnamic acid derivative with a phenyl group having at least one hydroxyl group or a pharmaceutically acceptable salt thereof as an effective ingredient.

2. Description of the prior art

AIDS (acquired immunodeficiency syndrome) has been spreading worldwide and constitute a social problem. At present, however, no effective AIDS preparation is known. For example, vaccinotherapy is being investigated. However, the denaturating properties of the proteinous portions of HIV-1 or HIV-2, an AIDS-causing virus, make it hard to establish reliable vaccinotherapy. Moreover, nucleic acid analogs such as azidothymidine are not acceptable cures in view of severe side-effects.

The inventors of the present invention have found that a substance with a strong anti-virus activity is contained in a water-soluble extract from ligneous materials and lignificated naturally occurring materials. Intense research was made into its components. As a result, a high molecular portion containing lignin has been found to have an anti-virus activity. Separately, it has been reported that lignosulfonic acid, an industrial waste in the pulp industry, has anti-AIDS virus activity. Isolation and purification of pure lignin from natural lignificated materials, though, is extremely difficult. The product is a mixture contaminated with hemicellulose or the like. Accordingly, there is a risk of side-effects due to the contaminants when it is used as a medicine. Furthermore, there is no evidence for the assumption that lignin consitutes an essential active structure closely related with the anti-virus activity or what type of lignin structure is more effective.

SUMMARY OF THE INVENTION

The inventors of the present invention have found a substance which is similar to naturally occuring lignificated material, but free from contaminants. The substance has anti-AIDS action. This substance is a dehydrogenation polymer of a cinnamic acid derivative.

An object of the present invention is the provision of a dehydrogenation polymer of a cinnamic acid derivative which is as an AIDS therapeutic agent, a process for its preparation and an AIDS therapeutic agent comprising the same polymer as an effective ingredient.

DETAILED DESCRIPTION OF THE INVENTION

Figure 1:
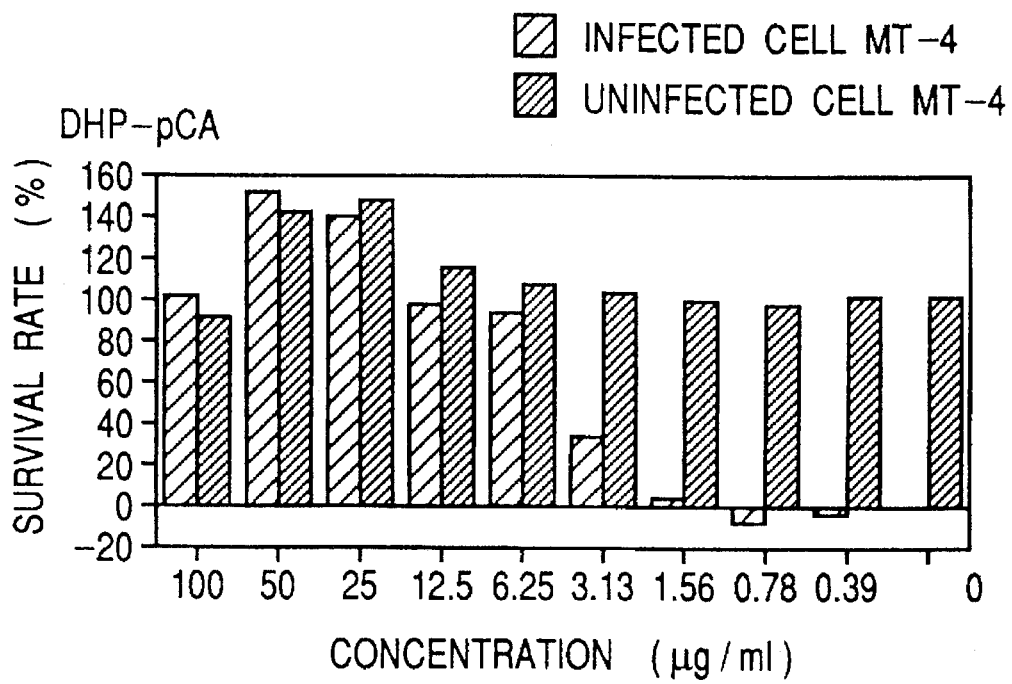
FIG. 1 is a graph showing the correlation between the concentration and activity of DRP-pCA.

The inventors of the present invention synthesized a wide variety of polymers of substituted phenylropanes which were investigated to find a dehydrogenation polymer of a cinnamic acid derivative having a phenyl group substituted with at least one hydroxyl group.

The cinnamic acid constituting the polymers of the present invention include cinnamic acid itself and its derivatives having a phenyl substituted with at least one hydroxyl group. Embodiments of such cinnamic acid derivatives are p-coumaric acid, ferulic acid, caffeic acid, umbellic acid, etc. The phenyl may have other substituents which do not present pharmacological issues. The synthesis of the polymers of the present invention may utilize salts, esters and anhydrides of the cinnamic acid derivatives.

The polymers of the present invention are synthesized by dehydrogenation polymerization of one or more of such cinnamic acid derivatives. The polymerization may be a copolymerization of a cinnamic acid derivative with a lignin component including p-coumary alcohol, coniferyl alcohol, cinnamyl alcohol, cinabil alcohol and so on.

The dehydrogenation polymerization is usually carried out using water as a solvent in the presence of a peroxidase and hydrogen peroxide.

Polymerization in the presence of a peroxidase and hydrogen peroxide may be carried out by, for example, two alternative ways. One is dropwise simultaneous addition of an aqueous solution of the cinnamic acid derivative and hydrogen peroxide to an aqueous solution of peroxidase. In the other way, a hydrogen peroxide solution is added dropwise to an aqueous solution containing both the cinnamic acid derivative and a peroxidase. The quantities of the peroxidase and hydrogen peroxide may be arbitrary so long as the selected quantities provide the polymer. Usually hydrogen peroxide is used in the range of 0.5 to 2.0 tools per tool of the cinnamic acid derivative. The quantity of the peroxidase used is within the range for usual enzyme reactions, and crude peroxidases may be used. The reaction temperature may range from 20° to 40° C., and the usual reaction time is 0.5 to 3 hours.

The polymers according to the present invention are a mixture of polymers of different degrees of polymerization. The molecular weight is not limited except if the polymer for pharmaceutical purposes, is desired to be a powdery material soluble in a neutral aqueous solution. Then the molecular weight distribution is preferred to Be within the range of around 800 to 150,000. The polymers within the purview of the present invention have a characteristic aspect in that they are of a network structure constructed by complicated polymerization through intermolecular convalent bonds of phenolic oxygens, phenyl carbons and substituent-bearing carbons contained in the monomer molecules (cinnamic acid derivatives), and they have carboxyl groups on branched chains. Part of the carboxyl groups are thought to form lactones or esters with adjacent phenolic hydroxyl groups in the molecules.

I. R. absorption spectrum evidence indicates that the polymers of the present invention have a structure possessing strong absorption bands in the absorption regions of hydrogen-OH bonds (3000 to 3600 $cm^{-1}$), carboxyl C=O bonds (1600 to 1720 $cm^{-1}$) and C—O bonds (100 to 1400 $cm^{-1}$). From I.V. absorption spectrum, the polymers are determined to have a structure which displays absorption maximum at around 280 nm, minimal absorption at around 260 nm, and another absorption gradually lessening to about 700 nm (end-absorption), with intensity of absorption at around 320 nm amplified in an alkaline solution. Furthermore, the polymers according to the present invent ion show strong proton N. M. R. Spectrum absorption and the spectrum is based on hydrogen (around 4 ppm) possessed by aromatic hydrogen (7 to 8 ppm), aliphatic double-bond hydrogen (5 to 6 ppm), O—CH hydrogen (4 to 5 ppm), and when monomers to be used (e.g., ferulic acid) have $OCH_3$ group, the spectrum is based on these hydrogens (around 4 ppm). In addition, the polymers according to the present invention show intensive E.S.R. spectrum of the powdery state absorption and the E.S.R. spectrum of powdery state is based on an organic free radical at a δ value of 2.003.

The polymers according to the present invention have an excellent anti-AIDS virus activity, are less toxic, and are useful as an agent for both treating and preventing AIDS.

The polymers according to the present invention may be administered to humans orally or parenterally, for example, by injection.

The preparations for oral administration include solids such as tablets, granules, powders, fine subtilaes or hard capsules as well as liquids, e.g., syrup preparations.

Such preparations may be made in the conventional manner. Illustratively, tablets, granules, powders and fine subtilaes are prepared by mixing a polymer of the present invention or its pharmaceutically acceptable salt with a conventional additive such as lactic acid, starch, crystalline cellulose, magnesium stearate, hydroxypropylcellulose or talc. Hard capsules may be made by filling capsules with the thus prepared powders or fine subtilaes appropriately.

The syrup preparations may be made by dissolving or suspending a polymer according to the present invention or a pharmaceutically acceptable salt thereof into an aqueous solution which contains sucrose, carboxymethyl cellulose, etc.

Injections may be prepared by aseptically encapsulating a polymer of the present invention or its pharmaceutically acceptable salt into physiological saline or another agent, for example, vegetable oil, oil emulsion, glycerol or the like.

The daily dose of the polymers according to the present invention usually is 1 to 300 mg per kg of body weight for the oral route, whereas the quantity is 0.1 to 100 mg for usual injection administration; the quantity may be given at one time or divided into two or three aliquots for intervallic administration a day.

The polymers of the present invention have a strong anti-AIDS virus activity and further have a low toxicity. Moreover, because of the presence of intermolecular carboxyl groups, they have an additional advantage in that water solubility is improved, and their preparations are easy to make. Accordingly, the polymers of the present invention are useful as both a therapeutic agent and a preventive agent against AIDS.

Explanation follows of the details of the present invention with reference to the particulars of the synthesis of the polymers and examples of their anti-AIDS virus activity. Preparation: Synthesis of the dehydrogenation polymers of the present invention Detailed explanation follows of the cases where the monomer used is p-coumaric acid, ferulic acid, caffeic acid or coniferyl alcohol.

Solutions A, B and C were prepared having the following compositions.

Solution A: One gram of a monomer to be polymerized was neutralized with 1N sodium hydroxide followed by addition of a 0.05M phosphate buffer solution (pH 8) to a total volume of 200 ml.

Solution B: Several ten milligrams of horseradish peroxidase was dissolved in 200 ml of a 0.05M phosphate buffer solution (pH 8).

Solution C: Hydrogen peroxide was dissolved in 200 ml of a 0.05 M phosphate buffer solution (pH 8), and the solution was diluted to 0.1%.

Polymerization Method 1 (Endwise method):

Two dropping funnels were attached to a three-neck flask containing solution B. Solutions A and C (in a ratio which provided 1.5 equivalents of hydrogen peroxide per the monomer used) were simultaneously added dropwise to solution B through separate funnels at 25° C. for 1 hour.

After the addition was completed, stirring was continued for an additional one hour, and then acetic acid was added to the solution to lower its pH to 3. The precipitated solids were collected by centrifugation, and then dissolved in water followed by dialysis and lyophilization.

Polymerization Method 2 (Bulk method):

Solution C was added dropwise to a solution prepared beforehand by mixing the solutions A and B, at 25° C. for 1 hour.

The procedures as in the Endwise method mentioned above were followed to yield a lyophilized sample of the same polymer.

Table 1 lists the reaction yields of the polymerization reactions, elementary analysis of the polymers of the present invention, U.V. absorbance, and the quantity of the organic free radicals estimated on the basis of the E.S.R. spectrum.

In the Table, DHP-pCA stands for the dehydrogenation polymer of p-coumaric acid, DHP-FA stands for the dehydrogenation polymer of ferulic acid, and DHP-CA stands for the dehydrogenation polymer Of caffeic acid.

TABLE 1

| Properties of the polymers of the present invention | | | | |
|---|---|---|---|---|
| Elementary analysis | | Reaction yields | U.V. absorbance intensity | Free radical (intensity of E.S.R.) |
| C | H | | | |
| Polymers prepared according to the Endwise method: | | | | |
| DHP-pCA 63.01 | 3.67 | 74% | 2.38 | 0.24 |
| DHP-FA 59.37 | 4.25 | 69% | 1.66 | 0.29 |
| DHP-CA 53.29 | 3.27 | 60% | 1.92 | 0.76 |
| Polymers prepared according to the Bulk method: | | | | |
| DHP-pCA 61.97 | 3.56 | 86% | 2.51 | 0.32 |
| DHP-FA 59.69 | 3.97 | 69% | 1.72 | 0.29 |
| DHP-CA 53.05 | 3.14 | 71% | 1.86 | 1.11 |

EXAMPLE 1

Activity against HIV-1 type viruses

1. Test compounds:

Illustrative demonstration follows of the results of the dehydrogenation polymer each of p-coumaric acid (DHP-pCA), ferulic acid (DHP-FA) and caffeic acid (DHP-CA).

2. Test procedure:

To a 96-well microtiter plate were added HTLV-IIIB-infected MT-4 cells ($2.5 \times 10^4$/well, MOI: 0.01) together with test compounds at various concentrations immediately after the infection. In the same manner virus-uninfected cells were cultured together with test compounds at various concentrations in order to determine the cytotoxicity of the test compounds to MT-4 cells. The culturing was carried out in a $CO_2$-incubator at 37° C. for 5 days. The survival cells were counted by the MTT method. The anti-virus activity was expressed in terms of the concentration at which 50% of the cell damage was prevented ($EC_{50}$) and the concentration at which 50% of cytotoxicity was prevented ($CC_{50}$). $CC_{50}$%/$EC_{50}$% (SI, selective index) was used as the index of effectiveness. (See Paunels et al., "J. Viro. Methods", vol. 20, pp.309–321, 1988.)

3. Test results

| Test compounds | $CC_{50}$ | $EC_{50}$ | SI |
|---|---|---|---|
| DHP-pCA | >100 | 3.85 | >26 |
| DHP-FA | >100 | 5.42 | >18 |
| DHP-CA | >100 | 7.10 | >12 |
| p-coumaric acid | >100 | >100 | ineffective |
| Caffeic acid | 2.1 | 3.1 | ineffective (<1) |
| Ferulic acid | >100 | >100 | inefective |

Figure 2:
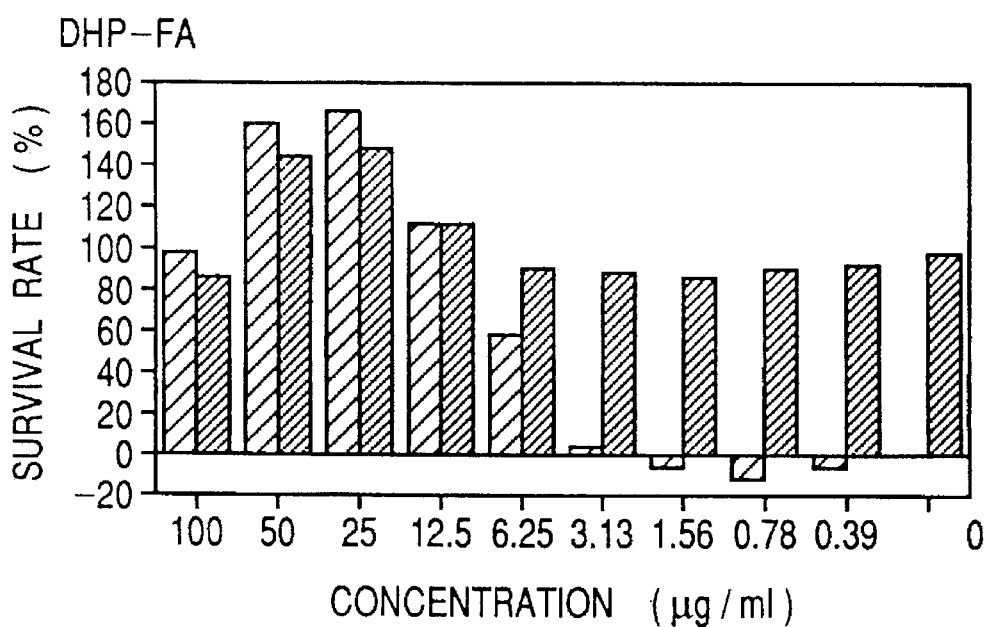
FIG. 2 is a graph showing the correlation between the concentration and activity of DHP-pFA.
Figure 3:
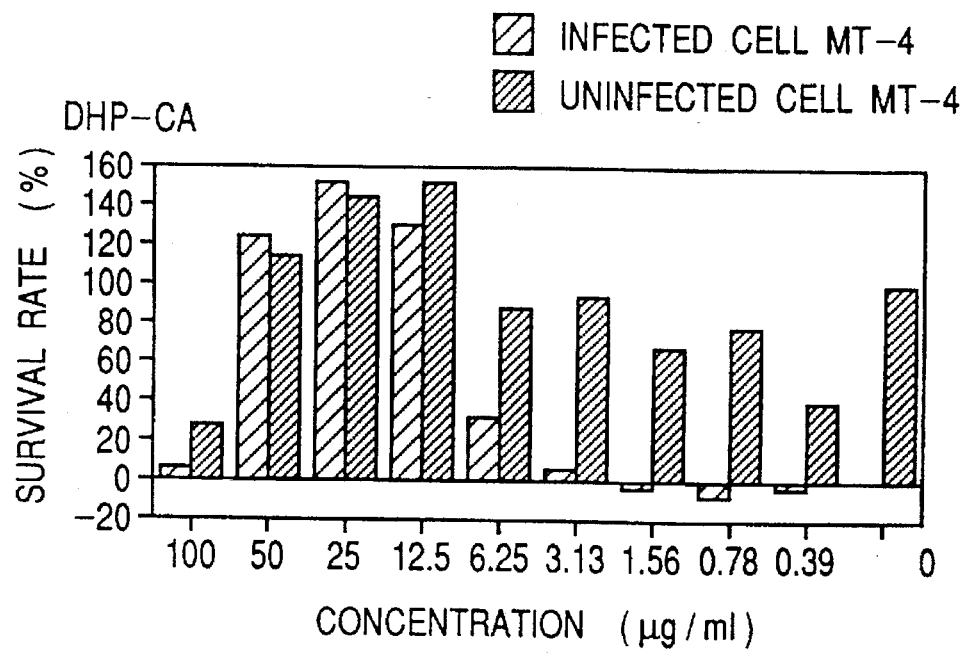
FIG. 3 is a graph showing the correlation between the concentration and activity of DHP-CA.
Figure 4:
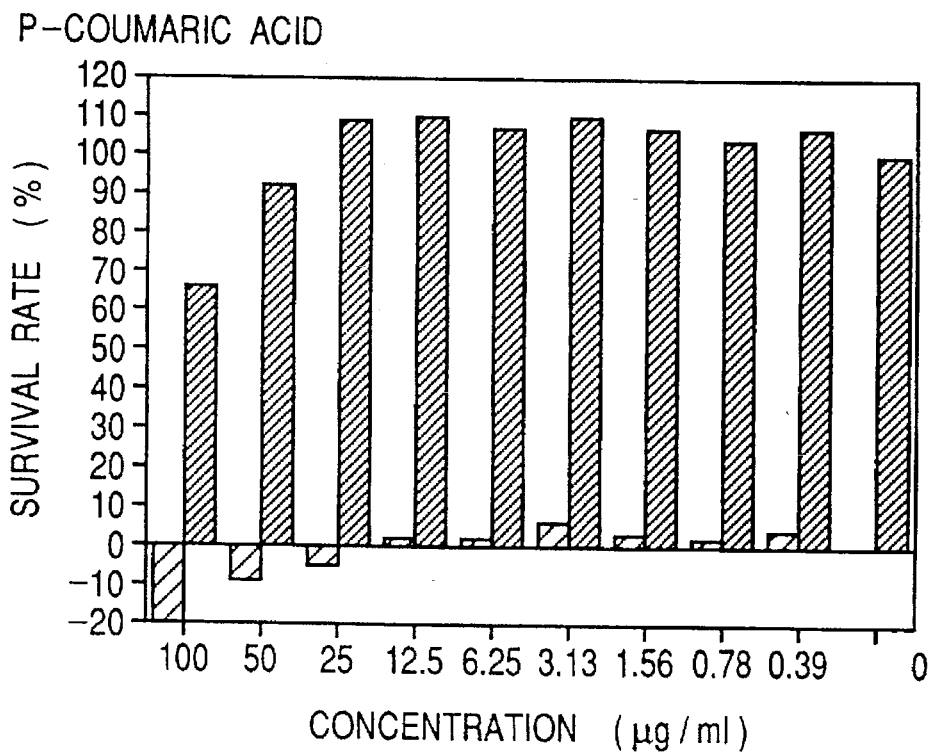
FIG. 4 is a graph showing the correlation between the concentration and activity of p-coumaric acid.
Figure 5:
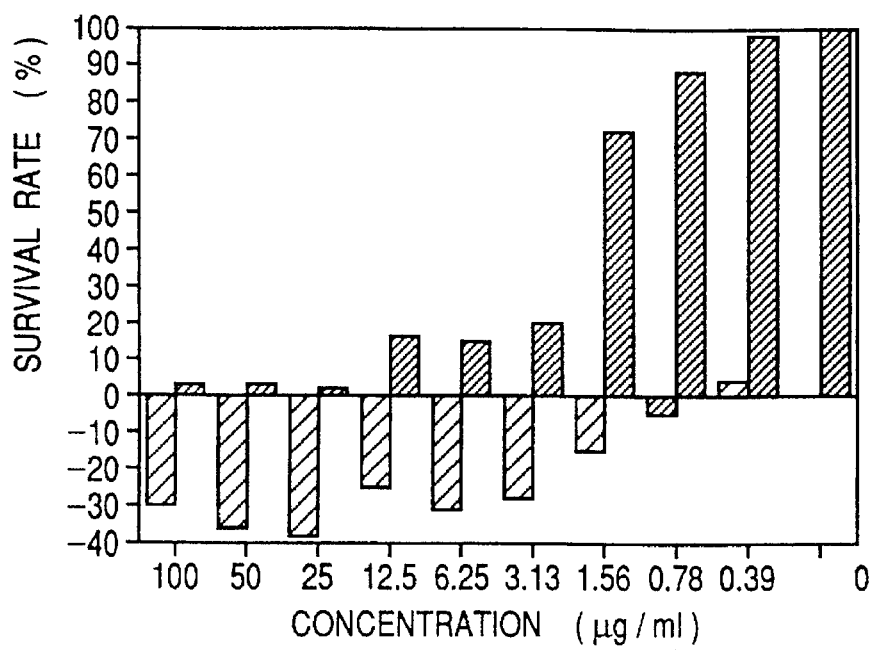
FIG. 5 is a graph showing the correlation between the concentration and activity of caffeic acid.
Figure 6:
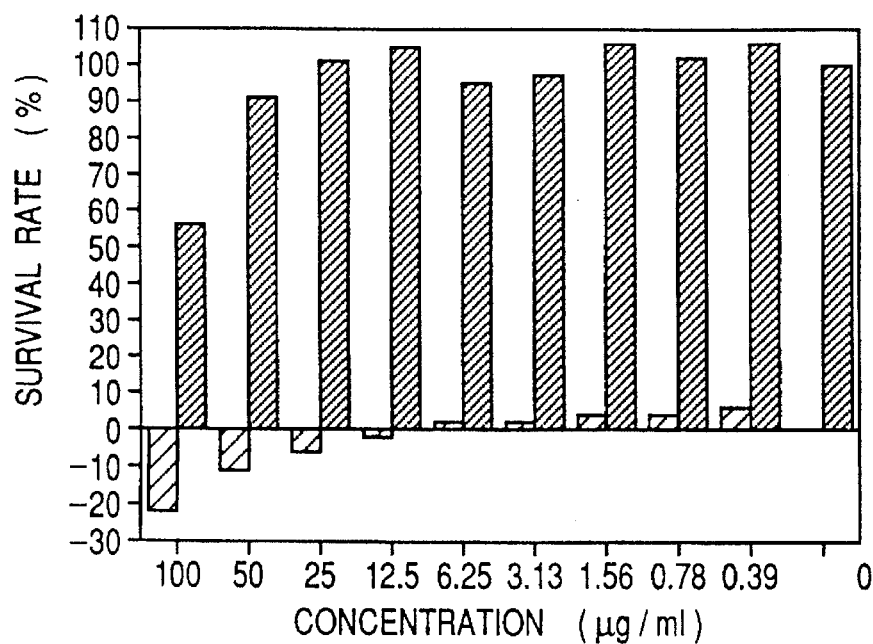
FIG. 6 is a graph showing the correlation between the concentration and activity of ferulic acid.

The correlation between concentration and action observed is shown in FIGS. 1 to 6 wherein the survival rate of the cells is represented by the longitudinal axis, while the axis of abscissa reflects concentration of the test compounds. The results reported in the above Table and FIGS. 1 to 3 show that the drugs according to the present invention have a remarkable antivirus activity.

EXAMPLE 2

Alternative evidence of inhibit growth of HIV-1 type viruses

1. Test compounds

Illustrative demonstration follows of the results of the dehydrogenation polymer each of p-coumaric acid (DHP-pCA), ferulic acid (DHP-FA) and caffeic acid (DHP-CA).

2. Test procedure:

To a 48-well plastic plate were added HIV-infected MT-4 cells (500 μl: $3 \times 10^5$ cell/ml) together with test compounds at various concentrations (500 μl). Culturing was carried out in $CO_2$-incubator at 37° C. for 5 days, and then the whole of the culture was transferred to a test tube for centrifugation. In order to determine the HIV membrane antigen positive rate by laser flow cytofluorography (FACS), the precipitated cells in free state were reacted with a primary antibody (human anti-HIV positive serum) or a secondary antibody (FITC-labelled anti-human IgG) for 1 hour. After the reaction was completed, the cells were washed and immobilized with formaldehyde to determine the antigen positive cells (F-cells) by FACS.

Using non-medicated HIV-infected MT-4 cells as the positive control and HIV-uninfected MT-4 cells as the negative control, the antigen positive rate (% control) for the cultures with the test compound added was calculated according to the following equation (see Nakashima et al., "Antimicrob. Agents Chemother.", p.311524, 1987).

Antigen positive rate=(A–C)/(B–C)
wherein

A: Medicated infected F-cells' rate

B: Nonmedicated infected F-cells' rate

C: Nonmedicated uninfected F-cells' rate.

3. Test results:

The test compounds showed not less than 90% inhibition rate at a concentration of 10 μg/ml or more. 50% effective rates ($EC_{50}$%) are shown below.

| Test compounds | $EC_{50}$ (μg/ml) |
|---|---|
| DHP-pCA | 0.83 |
| DHP-FA | 1.78 |
| DHP-CA | 2.56 |

EXAMPLE 3

Activity against HIV-2 type viruses

1. Test compound: Dehydrogenation polymer of caffeic acid (DHP-CA)

2. Test procedures:

To a 96-well microtiter plate were added HIV-2RODinfected MT-4 cells ($2.5 \times 10^4$ cells/well, MOI: 0.01) together with test compounds at various concentrations immediately after the infection. In the same manner, virus-uninfected cells were cultured together with the compounds at various concentrations in order to determine the cytotoxicity of the test compounds to MT-4 cells. Culturing was carried out in a $CO_2$-incubator at 37° C. for 5 days, an survival cells were counted by the MTT method. The anti-virus activity was expressed in terms of the concentration at which 50% of the cell damage was prevented ($EC_{50}$%) and regarding the concentration at which 50% of the cytotoxicity was prevented $CC_{50}$). $CC_{50}$%/$EC_{50}$% (SI, selective index) was used as the index of effectiveness. (See Paunels et al., "J. Viro. Methods", vol. 20, pp. 309–321, 1988.)

3. Test results:

| Test compounds | $CC_{50}$ | $EC_{50}$ | SI |
|---|---|---|---|
| DHP-CA | 174 | 5.07 | 34 |

What is claimed is:

1. An AIDS therapeutic agent comprising:
    a pharmaceutically effective amount of a polymer shown to be effective against HIV-1 and 2 viruses in MT-4 cell tests obtained by polymerizing in the presence of hydrogen peroxide and peroxidase or its pharmaceutically acceptable salt a cinnamic acid derivative represented by the formula:

R—CH=CH—COOH 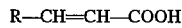

where R is a phenyl substituted with at least one hydroxyl group; and
    a pharmaceutically effective carrier.

2. The AIDS therapeutic agent of claim 1, wherein said cinnamic acid derivative is selected from the group consisting of p-coumaric acid, ferulic acid and caffeic acid.

3. The therapeutic agent of claim 1, wherein said polymer comprises a copolymer of said cinnamic acid derivative with a lignin component.

4. The therapeutic agent of claim 3, wherein said lignin component is selected from the group consisting of p-coumaryl alcohol, coniferyl alcohol and cinnamyl alcohol.

5. The therapeutic agent of claim 1, comprising a mixture of said polymers wherein said polymers have cinnamic acid derivatives of different degrees of polymerization.

6. The therapeutic agent of claim 5, wherein said mixture of polymers has a molecular weight distribution in the range of about 800 to 150,000.

7. The therapeutic agent of claim 1, wherein said polymer is characterized by a network structure having intermolecular covalent bonds and branch chains having carboxyl groups.

8. The therapeutic agent according to claim 1, wherein said effective amount is an AIDS treatment or prophylaxis effective amount.

9. A method of treatment or prophylaxis, comprising administering an HIV treatment or prophylaxis effective amount of the therapeutic agent of claim 1.

10. The method according to claim 9, comprising administering said therapeutic agent orally or parenterally.

11. The method according to claim 9, comprising administering said therapeutic agent to a human host infected with HIV.

12. The method according to claim 11, comprising administering 1 to 300 mg/kg of said therapeutic agent based on body weight of said host.

13. The method according to claim 11, comprising administering 0.1 to 100 mg/kg of said therapeutic agent based on body weight of a host.

14. The method according to claim 9, comprising administering said therapeutic agent by injection.

15. The method according to claim 9, wherein said therapeutic agent comprises a cinnamic acid derivative selected from the group consisting of coumaric acid, ferulic acid, caffeic acid and umbellic acid.

16. The method according to claim 9, wherein said therapeutic agent comprises a copolymer of said cinnamic acid derivative with a lignin component.

17. The method according to claim 16, wherein said lignin component is selected from the group consisting of p-coumaryl alcohol, coniferyl alcohol and cinnamyl alcohol.

18. The method according to claim 9, wherein said therapeutic agent comprises a mixture of polymers of said cinnamic acid derivatives wherein said polymers have different degrees of polymerization.

19. The method according to claim 18, wherein said mixture of polymers has a molecular weight distribution in the range of about 800 to 150,000.

20. The method according to claim 9 wherein said polymer is characterized by a network structure having intermolecular covalent bonds and branch chains having carboxyl groups.

21. A composition comprising:
a polymer shown to be effective against HIV-1 and viruses in MT-4 cell tests obtained by polymerizing in the presence of hydrogen peroxide and peroxidase or its pharmaceutically acceptable salt a cinnamic acid derivative represented by the formula:

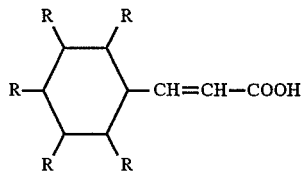

where R is independently H, OH or OCH$_3$ with the proviso that at least one R is OH; and
pharmaceutically effective carrier.

22. The polymer of claim 21, comprising a pharmaceutically acceptable salt of said polymer.

23. The polymer of claim 21 wherein said cinnamic acid derivative is selected from the group consisting of p-coumaric acid, ferulic acid and caffeic acid.

24. The polymer of claim 21, characterized by a network structure having intermolecular covalent bonds and branch chains having carboxyl groups.

25. The polymer of claim 21, comprising a copolymer of said cinnamic acid derivative with a lignin component.

26. The polymer of claim 25, wherein said lignin component is selected from the group consisting of p-coumaryl alcohol, coniferyl alcohol and cinnamyl alcohol.

27. A mixture of polymers according to claim 21, said polymers having different degrees of polymerization.

28. The mixture of polymers according to claim 27, having a molecular weight distribution in the range of about 800 to 150,000.

29. The AIDS therapeutic agent as claimed in claim 1, wherein said polymer is obtained by reacting about one mol of said cinnamic acid derivative in the presence of 0.5 mol to 2.0 mols of said hydrogen peroxide at a reaction temperature of from 20° C. to 40° C. and a reaction time of from 0.5 hour to 3 hours.

30. The AIDS therapeutic agent of claim 1, wherein the polymer has a structure possessing strong absorption bands in the absorption regions of hydrogen OH bonds 3,000 to 3,600 cm$^{-1}$), carboxyl C=O bonds (1,600 to 1,720 cm$^{-1}$) and C—O bonds (100 to 1,400 cm$^{-1}$) in I.R. absorption spectrum, and it has an absorption maximum at around 280 nm, minimal absorption at about 260 nm and another absorption gradually lessening to about 700 nm (end-absorption) from I.V absorption spectrum.

31. The AIDS therapeutic agent of claim 2, wherein said polymer is obtained by reacting said acid in phosphate buffer solution in the presence of hydrogen peroxide and horseradish peroxidase.

32. The AIDS therapeutic agent of claim 31, wherein said phosphate buffer solution is about 0.1% hydrogen peroxide and about 10 milligrams of horseradish peroxidase.

33. The method of claim 9, comprising administering said therapeutic agent as a treatment against HIV-1 type viruses and HIV-2 type viruses.

34. A method of selecting an AIDS therapeutic agent comprising testing a polymer of claim 1 to determine effectiveness against HIV viruses in a living animal.

35. A method of treatment or prophylaxis, comprising administering to a host an HIV treatment or prophylaxis effective amount of an AIDS therapeutic agent selected by the method of claim 34.

* * * * *